United States Patent [19]

Sofia

[11] Patent Number: 5,082,861
[45] Date of Patent: Jan. 21, 1992

[54] METHOD FOR THE PREVENTION AND CONTROL OF EPILEPTIC SEIZURE ASSOCIATED WITH COMPLEX PARTIAL SEIZURES

[75] Inventor: R. Duane Sofia, Willingboro, N.J.

[73] Assignee: Carter-Wallace, Inc., New York, N.Y.

[21] Appl. No.: 624,041

[22] Filed: Dec. 7, 1990

Related U.S. Application Data

[63] Continuation-in-part of Ser. No. 412,964, Sep. 26, 1989, Pat. No. 4,978,680.

[51] Int. Cl.$^5$ .............................................. A61K 31/24
[52] U.S. Cl. ...................................................... 514/534
[58] Field of Search ......................................... 514/534

[56] References Cited

U.S. PATENT DOCUMENTS 4,868,327  9/1989  Stiefel .................................... 560/164

Primary Examiner—Stanley J. Friedman
Attorney, Agent, or Firm—Kevin B. Clarke

[57] ABSTRACT

A novel method for the prevention and control of epileptic seizures particulary in patients with uncontrolled complex partial seizures employing pharmaceutical compositions containing 2-phenyl-1,3-propanediol dicarbamate.

3 Claims, No Drawings

METHOD FOR THE PREVENTION AND CONTROL OF EPILEPTIC SEIZURE ASSOCIATED WITH COMPLEX PARTIAL SEIZURES

This is a continuation-in-part of copending application Ser. No. 07/412,964 filed on Sept. 26, 1989 now U.S. Pat. No. 4,978,680.

The present invention relates to pharmaceutical compositions containing 2-phenyl-1,3-propanediol dicarbamate as an active component and to methods for the prevention and control of epileptic seizures by the use of such compositions.

More particularly, the present invention further relates to methods for increasing epileptic seizure threshold and the prevention of epileptic seizure spread through the administration of therapeutic compositions which contain as an active ingredient 2-phenyl-1,3-propanediol dicarbamate commonly known as Felbamate.

Felbamate is a well known pharmaceutical compound having been described in U.S. Pat. Nos. 2,884,444 and 4,868,327.

Epilepsy, a disease which has been characterized as a paroxysmal, self-sustaining and self-limited cerebral dysrhythmia, genetic or acquired in origin and physiologic or organic in mechanism is generally divided into four main types based on the type of seizure that occurs in those afflicted with the disease.

Based on clinical and electroencephalographic observations, the four general subdivisions of epilepsy are:
1. Grand mal
2. Petit mal
3. Psychomotor
4. Autonomic Those afflicted with epilepsy may present with any one of or a mixture of the foregoing forms of the disease.

In theory, it is believed that antiepileptic drugs act to prevent or control seizures by acting on the seizure focus which may be a collection of pathologically altered neurons or normal cells having restricted vascular supply or an injured area in which the neurons of a nerve net have been destroyed.

Up to the present time, all drugs used in the treatment of epilepsy function as prophylactics against the symptoms of epilepsy, i.e., the reduction and control of epileptic seizures as opposed to being curatives.

Although it is generally recognized that approximately 50% of epileptic patients can be controlled with presently available antiepileptic medications, there is a continuing long felt need for more selective and less toxic antiepileptic drugs. The desiratum of the art has been to provide a non-toxic, non-sedative, long-acting and highly effective antiepileptic drugs.

Phenytoin and carbamazepine are presently the drugs of choice for control of both generalized tonic-clonic (grand mal) and complex partial (temporal lobe) epileptic seizures.

In addition to gingival hyperplasia and hirsutism peculiar to phenytoin, both drugs have been reported to induce cerebellar-vestibular effects, skin disorders, hepatic deficiencies and congenital abnormalities. The foregoing toxicity profile for both phenytoin and carbamazepine clearly demonstrates a need for less toxic substances for use as antiepileptic medications.

One of the objects of the present invention is to provide compositions for the treatment of epilepsy comprising felbamate as the active ingredient.

Another object of the present invention is to provide relatively non-toxic compositions effective to control or prevent epileptic seizures which have a unique spectrum of antiepileptic activity and which include felbamate as an active component.

A further object of the present invention is to provide compositions for the prevention and control of epileptic seizures which compositions are relatively non-toxic, have a high degree of effectiveness and continue to produce a therapeutic response over relatively long periods of time.

A still further object of the present invention is to provide methods of treatment in patients with complex partial epileptic seizures.

Moreover, it is an object of the present invention to provide methods for the prevention and control of epileptic seizures through the use of felbamate.

Accordingly, it has been found that felbamate chemically described as 2-phenyl-1,3-propanediol dicarbamate is a compound which has demonstrated superior properties when compared to prototype drugs, i.e., phenytoin with respect to increasing seizure threshold and prevention seizure spread.

The compositions for the treatment of epilepsy may take any of a variety of forms although they are intended primarily for oral use and are suitable for forming into pills, capsules and tablets by well-known practices. When the active ingredient is in the form of a solid, a typical tablet composition comprises 500 milligrams of 2-phenyl-1,3-propanediol dicarbamate intermixed in a dry pulverulent state with suitable solid carriers and diluents.

In general, an effective daily dose of the active ingredient is in the range of from about 100 milligrams to about 5 grams.

Solid carriers and diluents suitable for use include sugars such as lactose and sucrose; cellulose derivatives such as carboxymethyl cellulose, ethyl cellulose, methyl cellulose, etc., gelatin including hard and soft gelatin capsules, talc, cornstarch, stearic acid and magnesium stearate.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets. However, for convenience in manufacturing and ease of administration, it is preferable that each dosage form contains at least 25 milligrams and up to 500 milligrams of 2-phenyl-1,3-propanediol dicarbamate per unit dosage form.

EXAMPLE 1

2-phenyl-1,3-propanediol dicarbamate is constituted into 500 mg. dosage units by encapsulation without an adjuvant into hard gelatin capsules. The yield from 1000 g. of 2-phenyl-1,3-propanediol dicarbamate is about 2000 capsules each containing 500 mg. of medicament.

EXAMPLE 2

A tableting formulation is prepared as follows:
83 g. 2-phenyl-1,3-propanediol dicarbamate
13 g. powdered sugar with 3% starch
76 g. corn syrup q.s. water
13 g. talc U.S.P. powdered Italian
3 g. magnesium stearate
q.s. alcohol
flavoring The formulation is compressed into tablets, each containing 200 mg. of 2-phenyl-1,3-propanediol dicarbamate. The yield is about 1750 tablets.

It has been found that the antiepileptic spectrum of Felbamate is effective in the treatment of complex partial and secondarily generalized seizures, seizure types frequently resistant to antiepileptic drug therapy. Felbamate has been found to abolish the hind limb tonic extensor phase of maximal electroshock seizures in laboratory animals and to elevate the threshold to seizures induced chemically by subcutaneous pentylenetetrazole. Felbamate has also been found to inhibit chemically-induced seizures secondary to picrotoxin. The mechanism of Felbamate's action is unknown.

Peak plasma concentration of Felbamate occurs from 1 to 3 hours after oral ingestion. In man approximately 90% of the dose of felbamate is recoverable in urine over a 10 day period. The major metabolic pathways in both animals and man are hydroxylation and conjugation.

Generally, antiepileptic drug clinical trials in patients with uncontrolled complex partial seizures and secondarily generalized seizures present difficulties since such patients may be taking one or more antiepileptic drugs which cannot usually be tapered without inducing clinically unacceptable seizure exacerbation; on the other hand, if concomitant drug administration is permitted, it may lead to pharmacologic interactions which can either vitiate the interpretation of a clinical trial, or lead to unacceptable toxicity.

In order to demonstrate the effectiveness of felbamate and, in order to overcome these obstacles as far as possible, the following procedure is followed: All patients are stabilized on carbamazepine, a present drug of choice in control of temporal lobe and grand mal epilepsy, before entry. Maintenance carbamazepine therapy is thought to give patients a reasonable degree of seizure control throughout the study, reduce the chance of drug interactions, and to allow a reasonable opportunity for felbamate to show its effect. A baseline period is used to exclude patients with evidence of seizure clustering. To ensure accurate recording of seizures, the patients remain in the hospital throughout the trial.

The study begins with a stabilization period, during which patients' therapy is adjusted to carbamazepine alone. Stabilization is considered to be achieved when the patient has two morning plasma levels of carbamazepine in the range of 4-16 milligrams per liter (mg/L).

Following stabilization, patients are admitted to the hospital for a three week baseline period. In order to qualify for randomization, patients must have at least six seizures during baseline, with at least one seizure in every week, and at least two weeks with two or more seizures.

Patients who meet the criterion are randomized at the end of baseline to one of four treatment sequences: felbamate-placebo-felbamate, felbamate-placebo-placebo, placebo-felbamate-placebo, and placebo-felbamate-felbamate or for short FPF, FPP, PFP and PFF. The treatments are administered over the course of alternating titration and analysis periods, each lasting two weeks. During the first titration period, the patient received gradually increasing doses of felbamate or placebo. The target felbamate dose was 3000 mg/day (maximum 50/mg/kg/day). The patient was then observed on a steady dose for a two week analysis period. This was followed by two more titration-analysis period pairs.

The study design called for 28 completed patients (7 in each arm) and a one-sided test of the hypothesis of no felbamate effect. The study was planned to have a power of 0.71 to detect a 50% reduction in seizure frequency due to felbamate, at a significance level of 0.05. However the observed variability in the data was less than the value used in planning the study, so the actual power to detect a 50% reduction was over 0.95.

Felbamate has a very favorable preclinical profile characterized by a substantial margin of safety (protective index 16.9–19.1). The following example presents the results from a double-blind randomized clinical trial in patients with partial seizures. Criteria for patient entry into the study were 4 or more complex partial seizures per month in spite of treatment with both phenytoin and carbamazepine.

EXAMPLE 3

Fifty-six patients (mean age 31.4 years; male=32, female=24) completed the study. The mean seizure frequencies for the eight week periods analyzed were: baseline=39.8; felbamate=34.9; placebo=40.2. Felbamate was significantly superior to placebo by percent seizure reduction (P=0.018) and truncated percent seizure reduction (P=0.007).

The mean felbamate dose was 2300 mg/day. Plasma felbamate concentrations ranged from 18.4 to 51.9, mean=32.5 mg/ml.

Adverse effects were minor and consisted of nausea and CNS effects.

In patients with complex partial seizures, the entry criteria required at least six seizures in a three week baseline period (and no more than one week with a single seizure) on carbamazepine alone. Twenty eight subjects were tested as demonstrated in Example 4.

EXAMPLE 4

The daily dose of 50 milligrams per kilogram (maximum 3000 mg) felbamate per day was well-tolerated by all 28 completers. Only mild side effects were encountered during the trial. Felbamate reduced carbamazepine level (P 0.0001; 95% confidence interval −28%, −20%). There was no significant difference in seizure frequency between placebo and felbamate periods (one-sided P=0.172).

The superiority of felbamate over placebo in a population of persons with severely refractory epilepsy indicates this medication to be a major antiepileptic agent.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A composition in dosage unit form for the treatment of partial complex seizures comprising a gelatin capsule containing about 25 to 500 milligrams 2-phenyl-1,3-propanediol dicarbamate.

2. A tableted composition in dosage unit form for the treatment of partial complex seizures comprising a solid pharmaceutical carrier and about 25 to about 500 milligrams of 2-phenyl-1,3-propanediol dicarbamate.

3. A method for treating partial complex seizures which comprises administering to a warm-blooded animal in need of such treatment 2-phenyl-1,3-propanediol dicarbamate in a daily dosage of from about 100 milligrams to about 5 grams.

* * * * *

(12) EX PARTE REEXAMINATION CERTIFICATE (6293rd)
United States Patent
Sofia

(10) Number: US 5,082,861 C1
(45) Certificate Issued: Jul. 15, 2008

(54) METHOD FOR THE PREVENTION AND CONTROL OF EPILEPTIC SEIZURE ASSOCIATED WITH COMPLEX PARTIAL SEIZURES

(75) Inventor: R. Duane Sofia, Willingboro, NJ (US)

(73) Assignee: Medpointe Healthcare Inc., Somerset, NJ (US)

Reexamination Request:
No. 90/007,992, Mar. 30, 2006

Reexamination Certificate for:
Patent No.: 5,082,861
Issued: Jan. 21, 1992
Appl. No.: 07/624,041
Filed: Dec. 7, 1990

Related U.S. Application Data

(63) Continuation-in-part of application No. 07/412,964, filed on Sep. 26, 1989, now Pat. No. 4,978,680.

(51) Int. Cl.
*A61K 31/21* (2006.01)
*A61K 31/27* (2006.01)

(52) U.S. Cl. .................................... 514/534

(58) Field of Classification Search .............. None
See application file for complete search history.

(56) References Cited

U.S. PATENT DOCUMENTS 2,724,720 A   11/1955   Berger
2,884,444 A   4/1959   Berger

OTHER PUBLICATIONS

A.J. Wilensky et al., Pharmacokinetics of W–544 (ADD 03055) in Epileptic Patients, 26 Epilepsia 602 (1985) (Raven Press, New York).
Ewart A. Swinyard et al., "Comparative Anticonvulsant Activity and Neurotoxicity . . . ," 27 Epilepsia 27 (1986) (New York City).
Ewart A. Swinyard et al., "The Effect of Chronic Felbamate Administration . . . ," 28 Epilepsia 295 (1987) (New York City).

*Primary Examiner*—Evelyn Huang

(57) ABSTRACT

A novel method for the prevention and control of epileptic seizures particulary in patients with uncontrolled complex partial seizures employing pharmaceutical compositions containing 2-phenyl-1,3-propanediol dicarbamate.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–3 are cancelled.

* * * * *